United States Patent
Unger et al.

(10) Patent No.: US 9,668,806 B2
(45) Date of Patent: Jun. 6, 2017

(54) SURGICAL FORCEPS INCLUDING A REMOVABLE STOP MEMBER

(75) Inventors: Jeffrey R. Unger, Longmont, CO (US); John R. Twomey, Longmont, CO (US); James D. Allen, IV, Broomfield, CO (US); Edward M. Chojin, Boulder, CO (US); Dylan R. Kingsley, Broomfield, CO (US); Kristel L. Ambrosius, Golden, CO (US)

(73) Assignee: COVIDIEN LP, Mansfield, MA (US)

( * ) Notice: Subject to any disclaimer, the term of this patent is extended or adjusted under 35 U.S.C. 154(b) by 1227 days.

(21) Appl. No.: 13/249,013

(22) Filed: Sep. 29, 2011

(65) Prior Publication Data

US 2013/0085496 A1  Apr. 4, 2013

(51) Int. Cl.
*A61B 18/14* (2006.01)
*B23P 11/00* (2006.01)
(Continued)

(52) U.S. Cl.
CPC ...... *A61B 18/1445* (2013.01); *A61B 18/1442* (2013.01); *A61B 2017/00526* (2013.01);
(Continued)

(58) Field of Classification Search
CPC ........ A61B 18/1445; A61B 2018/0063; A61B 2018/1455; A61B 2018/1861;
(Continued)

(56) References Cited

U.S. PATENT DOCUMENTS

| D249,549 S | 9/1978 | Pike |
| D263,020 S | 2/1982 | Rau, III |

(Continued)

FOREIGN PATENT DOCUMENTS

| CN | 201299462 | 9/2009 |
| DE | 2415263 | 10/1975 |

(Continued)

OTHER PUBLICATIONS

U.S. Appl. No. 08/926,869, filed Sep. 10, 1997, James G. Chandler.
(Continued)

*Primary Examiner* — Edward Moran
*Assistant Examiner* — Pamela M Bays

(57) ABSTRACT

A forceps includes an end effector assembly having first and second jaw members, each jaw member including a tissue sealing plate disposed thereon. One or both of the jaw members is movable relative to the other between a spaced-apart position and an approximated position for grasping tissue therebetween. One or both of the jaw members defines a first channel extending therethrough and an opening in the tissue sealing plate thereof that is aligned with the first channel. A stop member having a pre-determined configuration is removably engaged within the first channel. At least a portion of the stop member is configured to extend through the opening of the tissue sealing plate to define a minimum gap distance between the tissue sealing plates of the jaw members when the jaw members are disposed in the approximated position.

10 Claims, 6 Drawing Sheets

(51) Int. Cl.
*A61B 90/00* (2016.01)
*A61B 18/00* (2006.01)
*A61B 17/00* (2006.01)

(52) U.S. Cl.
CPC .......... *A61B 2018/0063* (2013.01); *A61B 2018/00083* (2013.01); *A61B 2018/00601* (2013.01); *A61B 2018/00607* (2013.01); *A61B 2018/1455* (2013.01); *A61B 2090/034* (2016.02); *Y10T 29/49826* (2015.01)

(58) Field of Classification Search
CPC ...... A61B 2018/1412; A61B 2019/304; A61B 2090/034; A61B 18/1442; A61B 2018/00601
USPC .................. 605/45, 51, 171; 606/45, 51, 171
See application file for complete search history.

(56) References Cited

U.S. PATENT DOCUMENTS

| | | |
|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| 5,403,312 A | 4/1995 | Yates et al. |
| D358,887 S | 5/1995 | Feinberg |
| D384,413 S | 9/1997 | Zlock et al. |
| 5,688,270 A | 11/1997 | Yates et al. |
| H1745 H | 8/1998 | Paraschac |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| 2006/0224158 A1* | 10/2006 | Odom et al. ............. 606/51 |
| 2008/0058802 A1* | 3/2008 | Couture ............ A61B 18/1442 606/48 |
| 2011/0071523 A1* | 3/2011 | Dickhans ................. 606/45 |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 10 2004 026179 | 12/2005 |
| DE | 20 2007 009165 | 10/2007 |
| DE | 20 2007 009317 | 10/2007 |
| DE | 20 2007 016233 | 3/2008 |
| DE | 19738457 | 1/2009 |
| DE | 10 2008 018406 | 7/2009 |
| EP | 1159926 | 12/2001 |
| JP | 61-501068 | 9/1984 |
| JP | 6-502328 | 3/1992 |
| JP | 5-5106 | 1/1993 |
| JP | 5-40112 | 2/1993 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-252263 | 10/1996 |
| JP | 8-317934 | 12/1996 |
| JP | 9-10223 | 1/1997 |
| JP | 9-122138 | 5/1997 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11-244298 | 9/1999 |
| JP | 2000-342599 | 12/2000 |
| JP | 2000-350732 | 12/2000 |
| JP | 2001-8944 | 1/2001 |
| JP | 2001-29356 | 2/2001 |
| JP | 2001-128990 | 5/2001 |
| JP | 2001-190564 | 7/2001 |
| JP | 2004-517668 | 6/2004 |
| JP | 2004-528869 | 9/2004 |
| SU | 401367 | 11/1974 |
| WO | WO 00/36986 | 6/2000 |
| WO | WO 01/15614 | 3/2001 |
| WO | WO 01/54604 | 8/2001 |
| WO | WO 2005/110264 | 11/2005 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed 6/920/00, Thomas P. Ryan.
U.S. Appl. No. 12/336,970, filed Dec. 17, 2008, Paul R. Sremeich.
U.S. Appl. No. 12/692,414, filed Jan. 22, 2010, Peter M. Mueller.
U.S. Appl. No. 12/696,592, filed Jan. 29, 2010, Jennifer S. Harper.
U.S. Appl. No. 12/696,857, filed Jan. 29, 2010, Edward M. Chojin.
U.S. Appl. No. 12/700,856, filed Feb. 5, 2010, James E. Krapohl.

(56) References Cited

OTHER PUBLICATIONS

U.S. Appl. No. 12/719,407, filed Mar. 8, 2010, Arlen J. Reschke.
U.S. Appl. No. 12/728,994, filed Mar. 22, 2010, Edward M. Chojin.
U.S. Appl. No. 12/748,028, filed Mar. 26, 2010, Jessica E.C. Olson.
U.S. Appl. No. 12/757,340, filed Apr. 9, 2010, Carine Hoarau.
U.S. Appl. No. 12/758,524, filed Apr. 12, 2010, Duane E. Kerr.
U.S. Appl. No. 12/759,551, filed Apr. 13, 2010, Glenn A. Horner.
U.S. Appl. No. 12/769,444, filed Apr. 28, 2010, Glenn A. Norner.
U.S. Appl. No. 12/770,369, filed Apr. 29, 2010, Glenn A. Horner.
U.S. Appl. No. 12/770,380, filed Apr. 29, 2010, Glenn A. Horner.
U.S. Appl. No. 12/770,387, filed Apr. 29, 2010, Glenn A. Horner.
U.S. Appl. No. 12/773,526, filed May 4, 2010, Duane E. Kerr.
U.S. Appl. No. 12/773,644, filed May 4, 2010, Thomas J. Gerhardt.
U.S. Appl. No. 12/786,589, filed May 25, 2010, Duane E. Kerr.
U.S. Appl. No. 12/791,112, filed Jun. 1, 2010, David M. Garrison.
U.S. Appl. No. 12/792,001, filed Jun. 2, 2010, Duane E. Kerr.
U.S. Appl. No. 12/792,008, filed Jun. 2, 2010, Duane E. Kerr.
U.S. Appl. No. 12/792,019, filed Jun. 2, 2010, Duane E. Kerr.
U.S. Appl. No. 12/792,038, filed Jun. 2, 2010, Glenn A. Horner.
U.S. Appl. No. 12/792,051, filed Jun. 2, 2010, David M. Garrison.
U.S. Appl. No. 12/792,068, filed Jun. 2, 2010, Glenn A. Horner.
U.S. Appl. No. 12/792,097, filed Jun. 2, 2010, Duane E. Kerr.
U.S. Appl. No. 12/792,262, filed Jun. 2, 2010, Jeffrey M. Roy.
U.S. Appl. No. 12/792,299, filed Jun. 2, 2010, Jeffrey M. Roy.
U.S. Appl. No. 12/792,330, filed Jun. 2, 2010, David M. Garrison.
U.S. Appl. No. 12/822,024, filed Jun. 23, 2010, Peter M. Mueller.
U.S. Appl. No. 12/821,253, filed Jun. 23, 2010, Edward M. Chojin.
U.S. Appl. No. 12/832,772, filed Jul. 8, 2010, Gary M. Couture.
U.S. Appl. No. 12/843,384, filed Jul. 26, 2010, David M. Garrison.
U.S. Appl. No. 12/845,203, filed Jul. 28, 2010, Gary M. Couture.
U.S. Appl. No. 12/853,896, filed Aug. 10, 2010, William H. Nau, Jr.
U.S. Appl. No. 12/859,896, filed Aug. 20, 2010, Peter M. Mueller.
U.S. Appl. No. 12/861,198, filed Aug. 23, 2010, James A. Gilbert.
U.S. Appl. No. 12/861,209, filed Aug. 23, 2010, William H. Nau, Jr.
U.S. Appl. No. 12/876,668, filed Sep. 7, 2010, Sara E. Anderson.
U.S. Appl. No. 12/876,680, filed Sep. 7, 2010, Peter M. Mueller.
U.S. Appl. No. 12/876,705, filed Sep. 7, 2010, Kristin D. Johnson.
U.S. Appl. No. 12/876,731, filed Sep. 7, 2010, Kristin D. Johnson.
U.S. Appl. No. 12/877,199, filed Sep. 8, 2010, Arlen J. Reschke.
U.S. Appl. No. 12/877,482, filed Sep. 8, 2010, Gary M. Couture.
U.S. Appl. No. 12/895,020, filed Sep. 30, 2010, Jeffrey M. Roy.
U.S. Appl. No. 12/896,100, filed Oct. 1, 2010, Ryan Artale.
U.S. Appl. No. 12/897,346, filed Oct. 4, 2010, Ryan Artale.
U.S. Appl. No. 12/906,672, filed Oct. 18, 2010, Kathy E. Rooks.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/006,538, filed Jan. 14, 2011, John W. Twomey.
U.S. Appl. No. 13/029,390, filed Feb. 17, 2011, Michael C. Moses.
U.S. Appl. No. 13/030,231, filed Feb. 18, 2011, Jeffrey M. Roy.
U.S. Appl. No. 13/050,182, filed Mar. 17, 2011, Glenn A. Horner.
U.S. Appl. No. 13/072,945, filed Mar. 28, 2011, Patrick L. Dumbauld.
U.S. Appl. No. 13/075,847, filed Mar. 30, 2011, Gary M. Couture.
U.S. Appl. No. 13/080,383, filed Apr. 5, 2011, David M. Garrison.
U.S. Appl. No. 13/083,962, filed Apr. 11, 2011, Michael C. Moses.
U.S. Appl. No. 13/085,144, filed Apr. 12, 2011, Keir Hart.
U.S. Appl. No. 13/089,779, filed Apr. 19, 2011, Yevgeniy Fedotov.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.

(56) References Cited

OTHER PUBLICATIONS

LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.

(56) References Cited

OTHER PUBLICATIONS

Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 185386.9 dated Jan. 10, 2011.
Int'l Search Report EP 10 185405.7 dated Jan. 5, 2011.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182022.3 dated Mar. 11, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 161117.4 dated Jun. 30, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

* cited by examiner

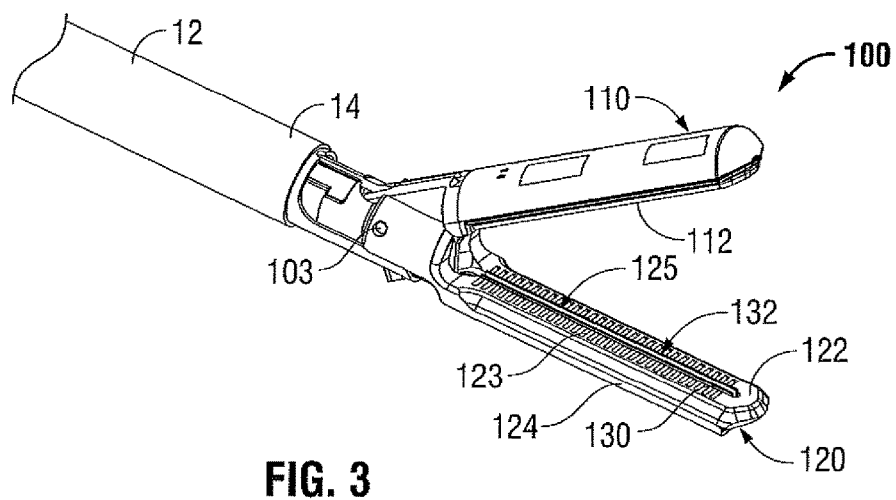
FIG. 3
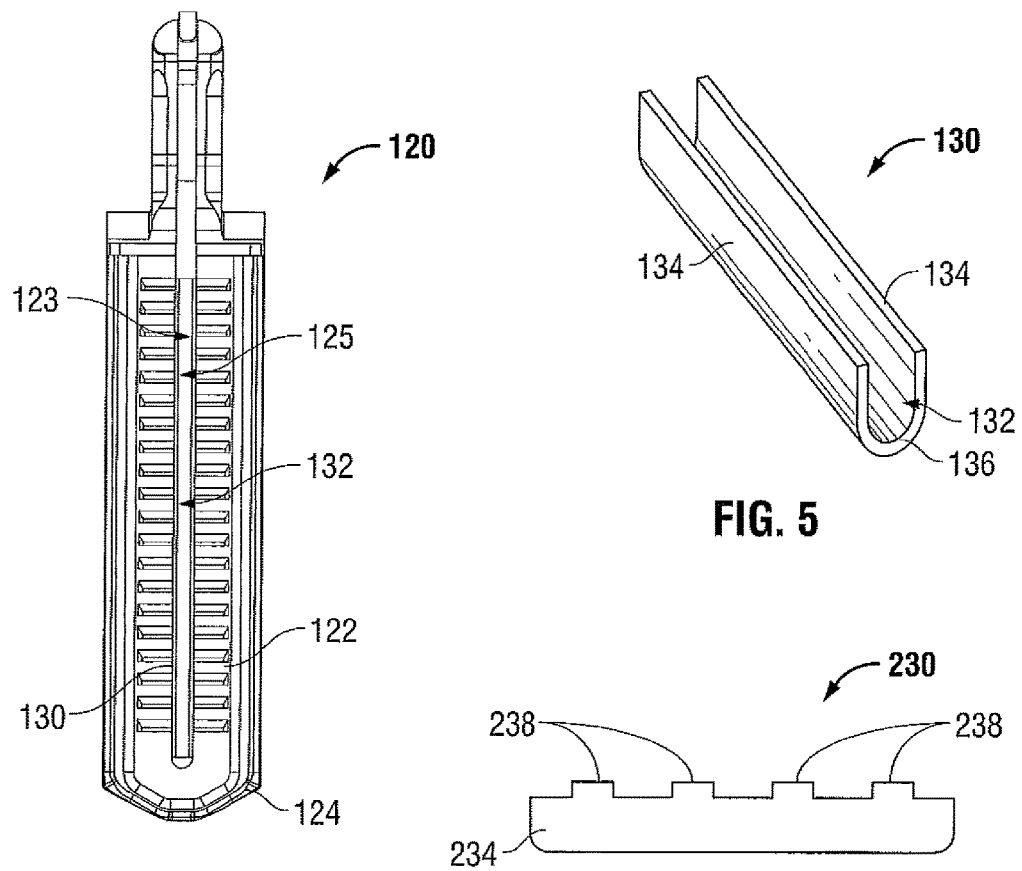
FIG. 4
FIG. 5
FIG. 6

SURGICAL FORCEPS INCLUDING A REMOVABLE STOP MEMBER

BACKGROUND

Technical Field

The present disclosure relates to surgical instruments and, more particularly, to surgical forceps for grasping, sealing, and/or dividing tissue.

Background of Related Art

A forceps is a plier-like instrument which relies on mechanical action between its jaws to grasp, clamp and constrict vessels or tissue. Electrosurgical forceps utilize both mechanical clamping action and electrical energy to affect hemostasis by heating tissue and blood vessels to coagulate and/or cauterize tissue. Certain surgical procedures require more than simply cauterizing tissue and rely on the unique combination of clamping pressure, precise electrosurgical energy control and gap distance (i.e., distance between opposing jaw members when closed about tissue) to "seal" tissue, vessels and certain vascular bundles. Typically, once a vessel is sealed, the surgeon has to accurately sever the vessel along the newly formed tissue seal. Accordingly, many vessel sealing instruments have been designed which incorporate a knife or blade member that effectively severs the tissue after forming a tissue seal.

SUMMARY

As used herein, the term "distal" refers to the portion that is being described which is further from a user, while the term "proximal" refers to the portion that is being described which is closer to a user.

In accordance with one aspect of the present disclosure, a forceps is provided. The forceps includes an end effector assembly having a pair of jaw members, each including an electrically-conductive tissue sealing plate disposed thereon. One (or both) of the jaw members is movable relative to the other between a spaced-apart position and an approximated position for grasping tissue therebetween. One (or both) of the jaw members defines a first channel extending therethrough and an opening defined within the tissue sealing plate thereof that is aligned with the first channel. A stop member is removably engaged within the first channel. A portion of the stop member is configured extend through the opening of the tissue sealing plate toward the other jaw member to define a minimum gap distance between the tissue sealing plates of the jaw members when the jaw members are disposed in the approximated position.

In one aspect, the minimum gap distance is in the range of about 0.001 inches to about 0.006 inches.

In another aspect, the stop member includes a second channel defined longitudinally therethrough. The second channel is configured to permit reciprocation of a knife blade therethrough for cutting tissue grasped between the jaw members. The second channel may define a pre-determined width configured in accordance with a width of the knife blade.

In yet another aspect, the second channel defines an arcuate configuration to define a correspondingly arcuate path for reciprocation of the knife blade therethrough.

In still yet another aspect, the stop member defines a substantially solid configuration to inhibit passage of tissue and fluids into the first channel.

In another aspect, the stop member is formed from an electrically insulative material.

In yet another aspect, the stop member includes a plurality of spaced-apart stop elements disposed along a length thereof. The stop elements are configured to extend through the opening of the tissue sealing plate toward the other jaw member to define the minimum gap distance between the jaw members.

In still another aspect, the stop member is formed from a resiliently compressible material that is configured to regulate a closure pressure between the jaw members. The closure pressure may be in the range of about 3 kg/cm$^2$ to about 16 kg/cm$^2$.

In still yet another embodiment, the stop member is removably engagable within the first channel of the at least one jaw member via friction-fitting.

A method of assembling a forceps for use in a surgical procedure is also provided in accordance with the present disclosure. The method includes providing an end effector assembly including a pair of jaw members. One or both of the jaw members is movable relative to the other between a spaced-apart position and an approximated position for grasping tissue therebetween. Each jaw member includes an electrically-conductive tissue sealing plate disposed thereon. One or both of the jaw members defines a first channel extending longitudinally therethrough. The tissue sealing plate of that jaw member defines an opening therethrough in alignment with the first channel. The method further includes selecting a stop member in accordance with the surgical procedure to be performed and engaging the selected stop member within the first channel. The stop member is configured to define a minimum gap distance between the tissue sealing plates of the jaw members when the jaw members are disposed in the approximated position.

In one aspect, the stop member is selected in accordance with a pre-determined minimum gap distance between the tissue sealing plates of the jaw members.

In another aspect, the stop member includes a second channel defined longitudinally therethrough. The second channel is configured to permit reciprocation of a knife blade therethrough for cutting tissue grasped between the jaw members. The stop member may be selected in accordance with a width of the knife blade and/or a pre-determined knife path of the knife blade.

In yet another aspect, the stop member is selected to inhibit passage of tissue and fluids into the first channel.

In still another aspect, the stop member is selected in accordance with a pre-determined closure pressure between the jaw members.

BRIEF DESCRIPTION OF THE DRAWINGS

Various embodiments of the present disclosure are described herein with reference to the drawings wherein like reference numerals identify similar or identical elements:

FIG. 3 is an enlarged, perspective view of an embodiment of an end effector assembly configured for use with the forceps of FIG. 1 or 2;

FIG. 4 is a top view of a jaw member of the end effector assembly of FIG. 3;

FIG. 5 is a front, perspective view of one embodiment of a stop member configured for use with the end effector assembly of FIG. 3;

FIG. 6 is a side view of another embodiment of a stop member configured for use with the end effector assembly of FIG. 3;

FIG. 11B is a transverse, cross-sectional view of one of the jaw members of the end effector assembly of FIG. 3 shown including still yet another embodiment of a stop member disposed therein, the stop member extending a second distance from the tissue sealing plate of the jaw member.

DETAILED DESCRIPTION

Figure 1:
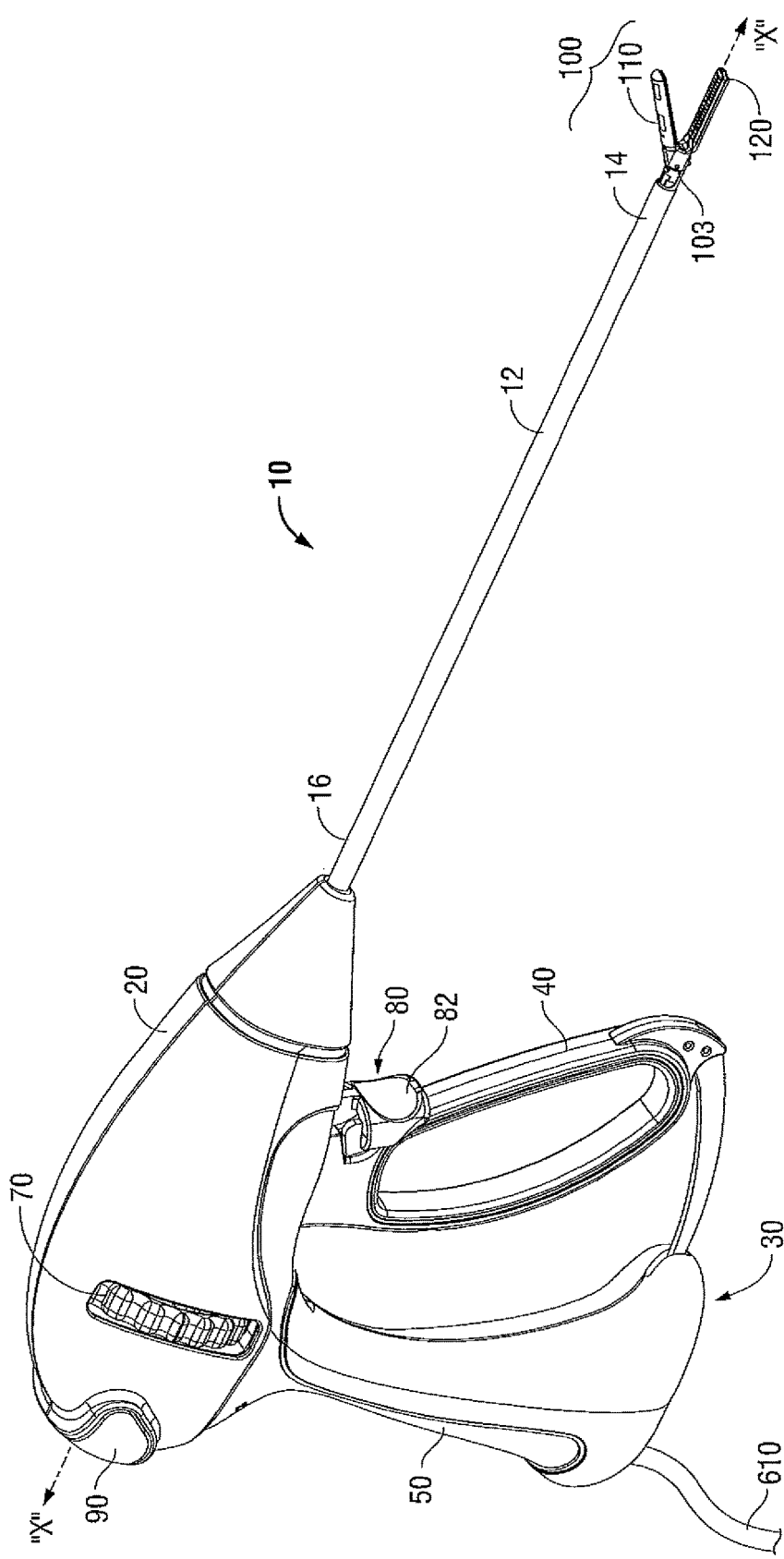
FIG. 1 is a front, perspective view of an endoscopic surgical forceps configured for use in accordance with the present disclosure.
Figure 2:
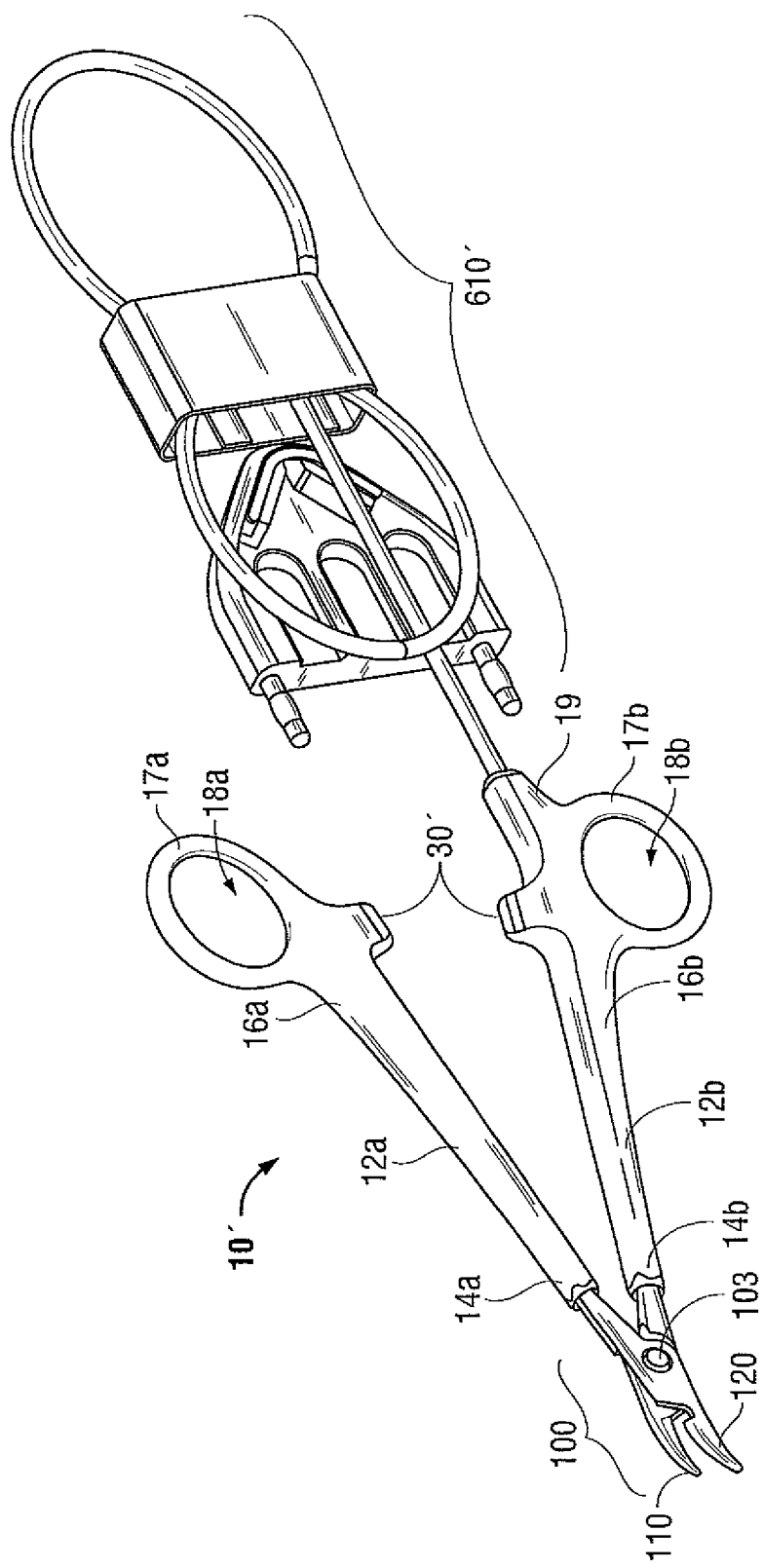
FIG. 2 is a front, perspective view of an open surgical forceps configured for use in accordance with the present disclosure.

Referring now to FIGS. 1 and 2, FIG. 1 depicts a forceps 10 for use in connection with endoscopic surgical procedures and FIG. 2 depicts an open forceps 10' contemplated for use in connection with traditional open surgical procedures. For the purposes herein, either an endoscopic instrument, e.g., forceps 10, or an open instrument, e.g., forceps 10', may be utilized in accordance with the present disclosure. Obviously, different electrical and mechanical connections and considerations apply to each particular type of instrument, however, the novel aspects with respect to the end effector assembly and its operating characteristics remain generally consistent with respect to both the open and endoscopic configurations.

Turning now to FIG. 1, an endoscopic forceps 10 is provided defining a longitudinal axis "X-X" and including a housing 20, a handle assembly 30, a rotating assembly 70, a trigger assembly 80 and an end effector assembly 100.

Forceps 10 further includes a shaft 12 having a distal end 14 configured to mechanically engage end effector assembly 100 and a proximal end 16 that mechanically engages housing 20. Forceps 10 also includes electrosurgical cable 610 that connects forceps 10 to a generator (not shown) or other suitable power source, although forceps 10 may alternatively be configured as a battery powered instrument. Cable 610 includes a wire (or wires) (not shown) extending therethrough that has sufficient length to extend through shaft 12 in order to provide electrical energy to at least one of the sealing plates 112, 122 (FIG. 3) of jaw members 110, 120, respectively, of end effector assembly 100, e.g., upon activation of activation switch 90.

With continued reference to FIG. 1, handle assembly 30 includes a fixed handle 50 and a movable handle 40. Fixed handle 50 is integrally associated with housing 20 and handle 40 is movable relative to fixed handle 50. Rotating assembly 70 is rotatable in either direction about longitudinal axis "X-X" to rotate end effector 100 about longitudinal axis "X-X." Housing 20 houses the internal working components of forceps 10.

End effector assembly 100 is shown attached at a distal end 14 of shaft 12 and includes a pair of opposing jaw members 110 and 120. Each of the jaw members 110 and 120 includes an electrically conductive tissue-sealing plate 112, 122 (FIG. 3), respectively. End effector assembly 100 is designed as a unilateral assembly, i.e., where jaw member 120 is fixed relative to shaft 12 and jaw member 110 is movable about pivot 103 relative to shaft 12 and fixed jaw member 120. However, end effector assembly 100 may alternatively be configured as a bilateral assembly, i.e., where both jaw member 110 and jaw member 120 are movable about pivot 103 relative to one another and to shaft 12. The particular features of end effector assembly 100 will be described in greater detail hereinbelow.

Figure 7A:
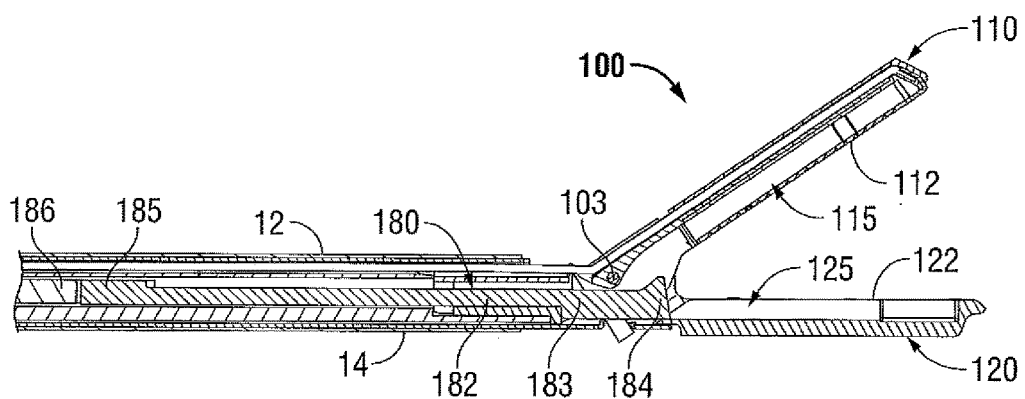
FIG. 7A is a longitudinal, cross-sectional view of the end effector assembly FIG. 3 with the jaw members disposed in a spaced-apart position.
Figure 7B:
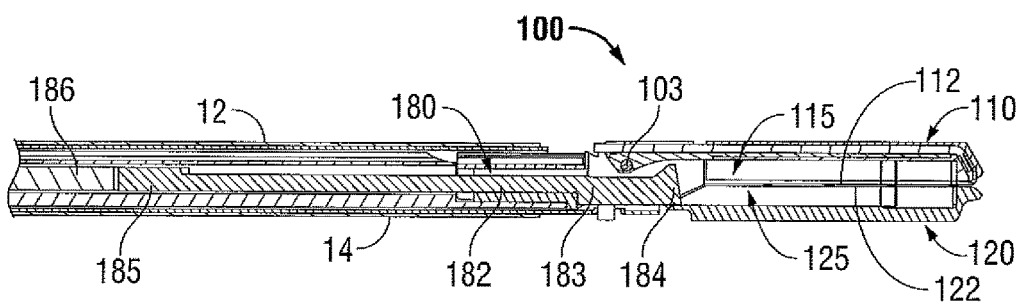
FIG. 7B is a longitudinal, cross-sectional view of the end effector assembly of FIG. 3 with the jaw members disposed in an approximated position and with a knife blade disposed in a retracted position.
Figure 7C:
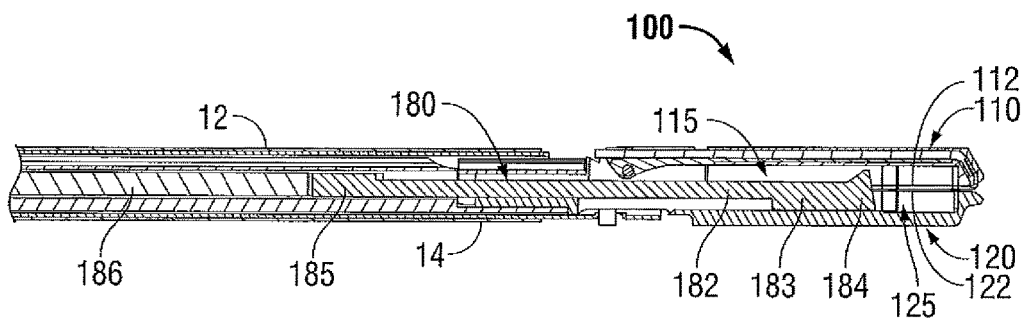
FIG. 7C is a longitudinal, cross-sectional view of the end effector assembly of FIG. 3 with the jaw members disposed in an approximated position and with the knife blade disposed in an extended position.

Referring momentarily to FIGS. 7A-7C, a knife assembly 180 is disposed within shaft 12 and a knife channel 115, 125 is defined within one or both jaw members 110, 120, respectively, to permit reciprocation of a knife blade 182 therethrough, e.g., via activation of a trigger 82 of trigger assembly 80 (FIG. 1). Knife assembly 180 includes a knife blade 182 defining a distal cutting edge 184 at the distal end 183 thereof. Knife blade 182 is coupled to a knife bar 186 at the proximal end 185 thereof. Knife bar 186 is selectively translatable, e.g., upon activation of trigger 82 of assembly 80 (FIG. 1), through shaft 12 and relative to end effector assembly 100 to translate knife blade 182 from the retracted position (FIG. 7B) to the extended position (FIG. 7C) to cut tissue disposed between jaw members 110, 120. Further, knife blade 182 may define various configurations, e.g., various different widths, cutting edge features, etc., to facilitate cutting different types of tissue or for use in various different surgical procedures. Accordingly, knife blade 182 may be removably coupled to knife bar 186 such that the user may select an appropriate knife blade 182 for use in conjunction with knife assembly 180 that is suitable for a particular surgical procedure to be performed.

With reference again to FIG. 1, movable handle 40 of handle assembly 30 is ultimately connected to a drive assembly (not shown) that, together, mechanically cooperate to impart movement of jaw members 110 and 120 between a spaced-apart position and an approximated position to grasp tissue disposed between sealing plates 112 and 122 (FIG. 3) of jaw members 110, 120, respectively. As shown in FIG. 1, movable handle 40 is initially spaced-apart from fixed handle 50 and, correspondingly, jaw members 110, 120 are in the spaced-apart position. Movable handle 40 is actuatable from this initial position to a depressed position corresponding to the approximated position of jaw members 110, 120 (see FIGS. 7B-7C).

Referring now to FIG. 2, an open forceps 10' is shown including two elongated shafts 12a and 12b, each having a proximal end 16a and 16b, and a distal end 14a and 14b, respectively. Similar to forceps 10 (FIG. 1), forceps 10' is configured for use with end effector assembly 100. More specifically, end effector assembly 100 is attached to distal ends 14a and 14b of shafts 12a and 12b, respectively. As mentioned above, end effector assembly 100 includes a pair of opposing jaw members 110 and 120 pivotably connected about pivot 103. Each shaft 12a and 12b includes a handle 17a and 17b disposed at the proximal end 16a and 16b thereof. Each handle 17a and 17b defines a finger hole 18a and 18b therethrough for receiving a finger of the user. As can be appreciated, finger holes 18a and 18b facilitate movement of the shafts 12a and 12b relative to one another which, in turn, pivots jaw members 110 and 120 from an open position, wherein the jaw members 110 and 120 are disposed in spaced-apart relation relative to one another, to a closed position, wherein the jaw members 110 and 120 cooperate to grasp tissue therebetween.

A ratchet 30' may be included for selectively locking the jaw members 110 and 120 relative to one another at various positions during pivoting. Ratchet 30' may include graduations or other visual markings that enable the user to easily and quickly ascertain and control the amount of closure force desired between the jaw members 110 and 120.

With continued reference to FIG. 2, one of the shafts, e.g., shaft 12b, includes a proximal shaft connector 19 that is designed to connect the forceps 10' to a source of electrosurgical energy such as an electrosurgical generator (not shown). Proximal shaft connector 19 secures an electrosurgical cable 610' to forceps 10' such that the user may selectively apply electrosurgical energy to the electrically conductive sealing plates 112 and 122 (FIG. 3) of jaw members 110 and 120, respectively, as needed.

Forceps 10' may further include knife assembly 180 (FIGS. 7A-7C) disposed within either of shafts 12a, 12b and knife channel 115, 125 (FIGS. 7A-7C) defined within one or both of jaw members 110, 120, respectively, to permit reciprocation of a knife blade 182 (FIGS. 7A-7C) therethrough.

Turning now to FIGS. 3-4, end effector assembly 100, including jaw members 110 and 120 is configured for use with either forceps 10 or forceps 10', discussed above, or any other suitable surgical instrument capable of pivoting jaw members 110, 120 relative to one another between a spaced-apart position and an approximated position for grasping tissue therebetween. However, for purposes of simplicity and consistency, end effector assembly 100 will be described hereinbelow with reference to forceps 10 only. Further, jaw members 110, 120 are substantially similar to one another and, thus, only the description of jaw member 120 will be detailed below for the purposed of brevity.

Jaw member 120, as shown in FIGS. 3-4, includes an outer jaw housing 124, an insulator 126 (FIGS. 8A-8B) disposed within outer jaw housing 124, and an electrically-conductive tissue-sealing plate 122 disposed atop insulator 126 (FIGS. 8A-8B) outer jaw housing 124 in opposed relation relative to tissue-sealing plate 112 of jaw member 110 such that, upon movement of jaw members 110, 120 to the approximated position (see FIGS. 7B-7C), tissue sealing plates 112, 122 of jaw members 110, 120, respectively, cooperate to grasp tissue therebetween. Insulator 126 (FIGS. 8A-8B) is configured to electrically isolate tissue sealing plate 122 from the other components of jaw member 120.

Jaw member 120 further includes blade channel 125 defined therein and extending longitudinally therealong. Blade channel 125, either alone, or in cooperation with blade channel 115 (FIGS. 7A-7C) of jaw member 110, is configured to permit reciprocation of knife blade 182 (FIGS. 7A-7C) therethrough, as will be described below. Tissue sealing plate 122 similarly includes a longitudinally-extending opening 123 defined therethrough that is aligned with blade channel 125 and is configured to permit passage of knife blade 182 (FIGS. 7A-7C) therethrough such that knife blade 182 (FIGS. 7A-7C) extends between jaw members 110, 120 to cut tissue grasped therebetween. More specifically, blade channel 125 is configured to receive a selected stop member therein, e.g., stop member 130, or any other stop member suitable for the surgical procedure to be performed, that extends through longitudinal opening 123 defined through tissue sealing plate 122 to define a minimum gap distance "G" (FIG. 8B) between sealing plates 112, 122 of jaw members 110, 120, respectively, when end effector assembly 100 is disposed in the approximated position. Knife blade 182 (FIGS. 7A-7C) is configured to extend through a channel 132 defined within stop member 130 which, in turn, is disposed within blade channel 125, as will be described in greater detail below.

Referring now to FIGS. 3-4, in conjunction with FIG. 5, as mentioned above, blade channel 125 of jaw member 120 and longitudinal opening 123 defined through tissue sealing plate 122 are configured to receive a stop member 130 therein. Stop member 130 defines an elongated, generally U-shaped configuration having a channel 132 extending longitudinally therethrough and a pair of opposed, spaced-apart walls 134 extending from base 136 of stop member 130 on either side of channel 132. Stop member 130 is formed from an electrically-insulative material and is configured for removable positioning within blade channel 125 of jaw member 120. Alternatively, stop member 130 may be secured within blade channel 125 of jaw member 120 in any suitable fashion, e.g., via adhesion, or may be monolithically formed with insulator 126 (FIGS. 8A-8B) of jaw member 120. Stop member 130 may be removably secured within blade channel 125 in any suitable fashion, e.g., friction-fitting (as shown), snap-fitting, etc. Accordingly, as will be described in greater detail below, the user may select a particular stop member, i.e., the user may select from, for example, stop members 130, 230 (FIG. 6), 330 (FIG. 9), 430 (FIG. 10A), 530 (FIG. 10B), 730 (FIG. 11A) 830 (FIG. 11B) and 930 (FIG. 12), that is appropriate for use for the specific surgical procedure to be performed. The selected stop member, e.g., stop member 130, may then be inserted into blade channel 125 of jaw member 120 in friction-fit engagement (or other suitable engagement) therewith for use in conjunction with end effector assembly 100.

With continued reference to FIGS. 3-4, channel 132 of stop member 130 is configured to permit passage of knife blade 182 (FIGS. 7A-7C) therethrough such that knife blade 182 (FIGS. 7A-7C) may be advanced through blade channel 125, to cut tissue disposed between jaw members 110, 120. The opposed walls 134 of stop member 130 are configured to extend a predetermined distance from tissue sealing plate 122 when disposed within blade channel 125 to define a minimum gap distance "G" (FIG. 8B) between sealing plates 112, 122 of jaw members 110, 120, respectively, when end effector assembly 100 is disposed in the approximated position, as will be described in greater detail below.

FIG. 6 shows another embodiment of a stop member 230 substantially similar to stop member 130 except that walls 234 of stop member 230 define an alternating protrusion-recess configuration. In this configuration, the protrusions 238 of stop member 230 (rather than the entire edge as in stop member 130) contact tissue sealing plate 112 (FIG. 8B), or any other suitable portion of jaw member 110 (FIG. 8B) to define a minimum gap distance "G" (FIG. 8B) between sealing plates 112, 122 of jaw members 110, 120, respectively. In other words, protrusions 238 form a plurality of spaced-apart stop elements 238 extending from walls 234 and disposed along the length of stop member 230 for defining the minimum gap distance "G" (FIG. 8B) between sealing plates 112, 122 of jaw members 110, 120, respectively. Stop member 230 is otherwise similar to stop member 130 and, thus, will not be described further herein for purposes of brevity.

With reference now to FIGS. 7A-7C and 8A-8B, the use and operation of end effector assembly 100 is described. Initially, the user selects a desired stop member for engagement within blade channel 125 defined within jaw member 120 (and/or blade channel 115 defined within jaw member 110). Various different embodiments of stop members, in addition to stop members 130, 230 (FIGS. 5, 6, respectively), that are configured for use with end effector assembly 100 to facilitate performing various different surgical procedures will be described below with reference to FIGS. 9-12. For the purposes herein, however, the use and operation of end effector assembly 100 will be described with reference to stop member 130 only, keeping in mind that the other embodiments of stop members disclosed herein may similarly be used in conjunction with end effector assembly 100.

Figure 8A:
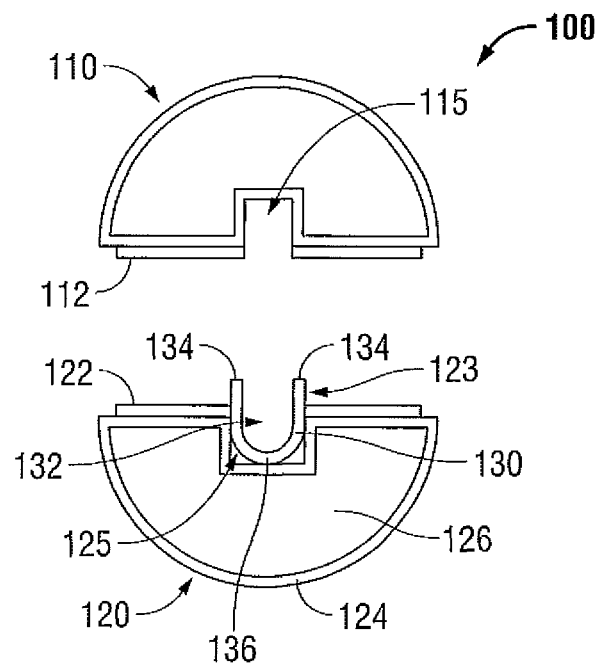
FIG. 8A is a transverse, cross-sectional view of the end effector assembly of FIG. 3 with the jaw members disposed in the spaced-apart position.
Figure 8B:
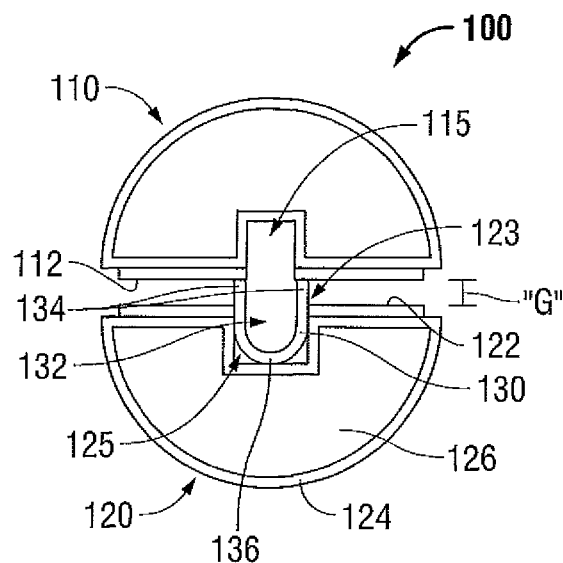
FIG. 8B is a transverse, cross-sectional view of the end effector assembly of FIG. 3 with the jaw members disposed in the approximated position.

In use, with stop member 130 engaged within blade channel 125 of jaw member 120 and with jaw members 110, 120 disposed in the spaced-apart position, as shown in FIGS. 7A and 8A, end effector assembly 100 is maneuvered into position such that tissue to be grasped, sealed, and/or cut, is disposed between jaw members 110, 120. Next, movable handle 40 (FIG. 1) is pulled proximally relative to fixed handle 50 (FIG. 1) such that jaw member 110 is pivoted about pivot 103 relative to jaw member 120 from the spaced-apart position to the approximated position to grasp tissue therebetween (see FIGS. 7B and 8B). In this approximated position, as best shown in FIG. 8B, walls 134 of stop member 130 extend from jaw member 120 into contact with tissue sealing plate 112 of jaw member 110, thereby defining a minimum gap distance "G" between tissue sealing plates 112, 122 of jaw members 110, 120, respectively. Typically, for tissue-sealing, the gap distance "G" between tissue sealing plates 112, 122 is in the range of about 0.001 inches to about 0.006 inches. Accordingly, walls 134 of stop member 130 may be configured to achieve a gap distance "G" within this range, or may be configured to achieve any other desired gap distance or range of gap distances.

Stop member 130 may also be formed at least partially from a resiliently compressible material to regulate the closure pressure between jaw members 110, 120. More specifically, the resiliently compressible configuration of stop member 130 facilitates achieving a desired gap distance "G" between sealing plates 112, 122 of jaw members 110, 120, respectively, in accordance with a pre-determined closure pressure, or range of closure pressures, between jaw members 110, 120 when grasping tissue therebetween. Typically, during tissue sealing, the closure pressure between jaw members 110, 120 is in the range of about 3 kg/cm$^2$ to about 16 kg/cm$^2$, although closure pressure ranges are also contemplated.

With jaw members 110, 120 disposed in the approximated position grasping tissue therebetween and defining the desired gap distance "G" therebetween, as discussed above, electrosurgical energy may be supplied, e.g., via activation of switch 90 (FIG. 1), to tissue-sealing plate 112 of jaw member 110 and/or tissue-sealing plate 122 of jaw member 120 and conducted through tissue to effect a tissue seal. Controlling the gap distance "G" between tissue sealing plates 112, 122 of jaw members 110, 120, respectively, during tissue sealing not only helps ensure adequate formation of a tissue seal, but also helps inhibit shorting or other damage as a result of contact between the opposed electrically-conductive tissue sealing plates 112, 122.

As shown in FIG. 7B-7C, once tissue sealing is complete (or to cut untreated tissue, where tissue sealing is not desired), knife blade 182 may then be advanced from the retracted position (FIG. 7B) to the extended position (FIG. 7C), e.g., via activation of trigger 82 of trigger assembly 80 (FIG. 1), and through blade channels 115, 125 of jaw members 110, 120, respectively, or, more specifically, through channel 132 of stop member 130, to cut tissue grasped between jaw members 110, 120. Thereafter, jaw members 110, 120 may be returned to the spaced-apart position (FIG. 7A) and removed from the surgical site, or the above-described process may be repeated to grasp, seal and/or divide additional tissue structures. Stop member 130 may then be removed from blade channel 125 of jaw member 120 and forceps 10 (FIG. 1) can be sterilized for reuse (with another stop member similar or different from stop member 130) or, in embodiments where forceps 10 is configured as a disposable instrument, forceps 10 may be discarded after use.

Turning now to FIGS. 9-12, different embodiments of stop members configured for use with end effector assembly 100 are shown. The stop members detailed hereinbelow are similar to stop members 130, 20, discussed above, and thus will only be discussed with respect to the differences therebetween and the specific features thereof that may be advantageous for use in one or more surgical procedures.

Figure 9:
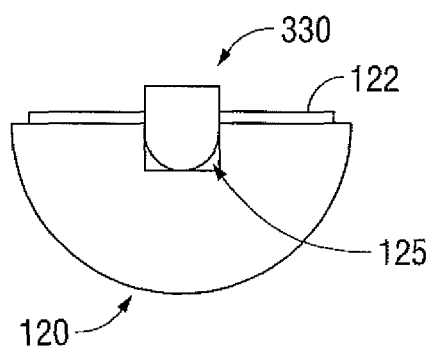
FIG. 9 is a transverse, cross-sectional view of one of the jaw members of the end effector assembly of FIG. 3 shown including another embodiment of a stop member disposed therein.

Referring now to FIG. 9, stop member 330 is shown disposed within blade channel 125 of jaw member 120. As shown, stop member 330 defines a generally u-shaped configuration to facilitate releasable frictional engagement within blade channel 125 of jaw member 120. However, rather than defining a channel extending therethrough, as in stop member 130 (FIG. 5), stop member 330 defines a continuous, solid configuration. Stop member 330 may be selected for use with end effector assembly 100 in surgical procedures where cutting tissue, e.g., with knife blade 182 of knife assembly 180 (FIGS. 7A-7C), is not required. In such a procedure, stop member 330, similar to stop member 130 (FIG. 5), operates to set a gap distance "G" (FIG. 8B) between the tissue sealing plates 112, 122 of jaw members 110, 120 (see FIG. 8B), respectively. Stop member 330 also inhibits tissue or other fluids from entering the unused blade channel 125.

Figure 10A:
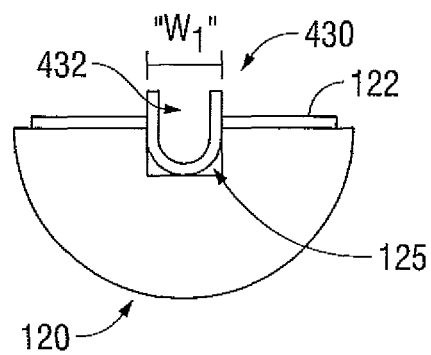
FIG. 10A is a transverse, cross-sectional view of one of the jaw members of the end effector assembly of FIG. 3 shown including another embodiment of a stop member disposed therein, the stop member including a channel defined therethrough having a first width.
Figure 10B:
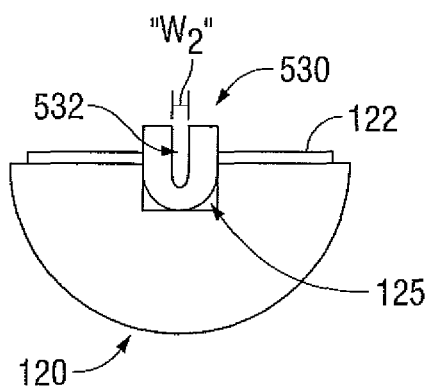

As shown in FIGS. 10A and 10B, stop members 430, 530, respectively are shown disposed within blade channel 125 of jaw member 120. Stop member 430, 530 are similar to stop member 130 (FIG. 5) and to one another, except that stop member 430 defines a channel 432 extending therethrough that defines a first width "W$_1$," while stop member 530 includes a channel 532 extending therethrough that defines a second width "W$_2$," that is smaller than width "W$_1$." As such, stop member 430 is best suited for use in conjunction with a knife blade 182 (FIGS. 7A-7C) having a relatively larger width, while stop member 530 is best suited for use in conjunction with a knife blade 182 (FIGS. 7A-7C) having a relatively narrower width. Conforming the width of the channel 432, 532 defined within the stop member 430, 530, respectively, helps ensure consistent and accurate translation of knife blade 182 (FIGS. 7A-7C) therethrough and helps inhibit blade splay as knife blade 182 (FIGS. 7A-7C) is advanced therethrough to cut tissue grasped between jaw members 110, 120 of end effector assembly 100 (FIG. 3).

Figure 11A:
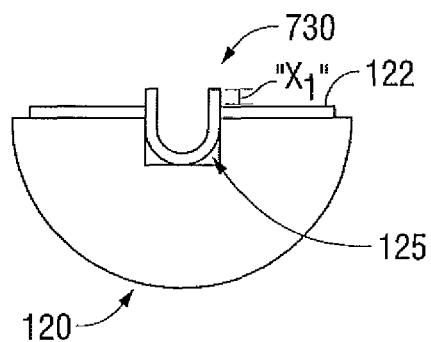
FIG. 11A is a transverse, cross-sectional view of one of the jaw members of the end effector assembly of FIG. 3 shown including still another embodiment of a stop member disposed therein, the stop member extending a first distance from the tissue sealing plate of the jaw member.
Figure 11B:
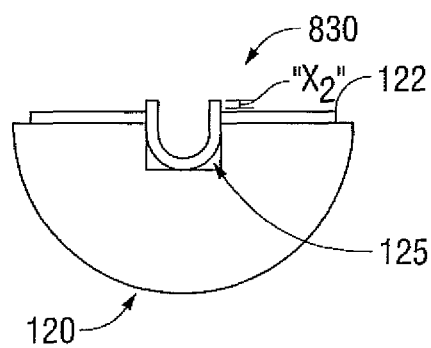
FIG. 11B is a transverse, cross-sectional view of one of the jaw members of the end effector assembly of FIG. 3 shown including yet another embodiment of a stop member disposed therein, the stop member including a channel defined therethrough having a second width.

With reference to FIGS. 11A and 11B, stop members 730, 830 are shown disposed within blade channel 125 of jaw member 120. Stop members 730, 830 are similar to stop member 130 and to one another, except that stop member 730 extends a first distance "$X_1$," from tissue sealing plate 122 of jaw member 120, while stop member 830 extends a second distance "$X_2$," that is smaller than distance "$X_1$," from tissue sealing plate 122 of jaw member 120. Accordingly, with stop members 730, 830 extending different distances "$X_1$" and "$X_2$," respectively, from tissue sealing plate 122 of jaw member 120, the gap distance "G" (FIG. 8B) formed between jaw members 110, 120 (FIG. 3) is varied depending on whether stop member 730 or stop member 830 is used in conjunction with end effector assembly 100. In other words, the user may select a desired stop member, e.g., stop member 730 or stop member 830, corresponding to a desired gap distance "G" (FIG. 8B) between jaw members 110, 120 (FIG. 3) during use. Alternatively, or additionally, stop members 730, 830 may be formed from different materials having varying degrees of compressibility such that a desired gap distance "G" (FIG. 8B) is achieved between sealing plates 112, 122 of jaw members 110, 120 (FIG. 8B), respectively, in accordance with the closure pressure therebetween.

Figure 12:
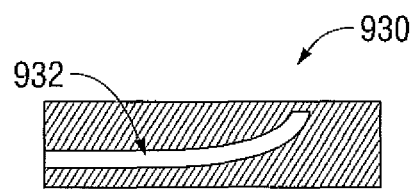
FIG. 12 is a top view of another embodiment of a stop member provided in accordance with the present disclosure.

Referring now to FIG. 12, stop member 930 is shown. Stop member 930 may be configured similarly to any of the stop members discussed above, except that channel 932 defined through stop member 930 defines a curved, or arcuate configuration, although other configurations are contemplated. Stop member 930 may be engaged within blade channel 125 of jaw member 120 (FIG. 3) for use in surgical procedures where it is advantageous to advance knife blade 182 (FIGS. 7A-7C) therethrough along a curved path (or other suitably-configured blade path) to facilitate cutting tissue grasped between jaw members 110, 120 (FIG. 3).

The stop members detailed above with reference to FIGS. 5-6 and 9-12 are examples of stop members that may be configured for use in conjunction with end effector assembly 100 depending on the particular surgical procedure to be performed. As can be appreciated, providing a replaceable stop member selected from a group of stop members having various different configurations allows the user to customize a single end effector assembly, e.g., end effector assembly 100, for use in various different procedures, e.g., procedures requiring cutting of tissue or procedures not requiring cutting of tissue, procedures wherein it is desirable to use a thicker or thinner knife blade, procedures wherein different gap distances "G" (FIG. 8B) are desired, procedures wherein it is desired to define a specific blade channel shape or configuration, etc., rather than requiring a different end effector assembly or surgical instrument for each different procedure to be performed.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A forceps, comprising:
an end effector assembly including a pair of jaw members, at least one of the jaw members movable relative to the other between a spaced-apart position and an approximated position for grasping tissue therebetween, each of the jaw members including an electrically-conductive tissue sealing plate disposed thereon, at least one of the jaw members defining a longitudinal axis extending from a proximal end to a distal end thereof and a first channel extending therethrough along the longitudinal axis, the tissue sealing plate of the at least one jaw member defining an opening therethrough in alignment with the first channel; and
a U-shaped stop member removably engaged within the first channel, the U-shaped stop member including a base portion disposed within the first channel and at least a portion extending from the base portion and configured to extend through the opening of the tissue sealing plate toward the other jaw member to define a minimum gap distance between the tissue sealing plates of the jaw members when the jaw members are disposed in the approximated position, wherein the base portion and the at least one portion extending from the base portion cooperate to define a second channel extending along the longitudinal axis, the second channel configured to permit reciprocation of a knife blade therethrough for cutting tissue grasped between the jaw members.

2. The forceps according to claim 1, wherein the minimum gap distance is in the range of about 0.001 inches to about 0.006 inches.

3. The forceps according to claim 1, wherein the second channel defines a pre-determined width configured in accordance with a width of the knife blade.

4. The forceps according to claim 1, wherein the second channel defines an arcuate configuration to define a correspondingly arcuate path for reciprocation of the knife blade therethrough.

5. The forceps according to claim 1, wherein the stop member defines a substantially solid configuration to inhibit passage of tissue and fluids into the first channel.

6. The forceps according to claim 1, wherein the stop member is formed from an electrically insulative material.

7. The forceps according to claim 1, wherein the stop member includes a plurality of spaced-apart stop elements disposed along a length of the stop member, the stop elements configured to extend through the opening of the tissue sealing plate toward the other jaw member to define the minimum gap distance between the jaw members.

8. The forceps according to claim 1, wherein the stop member is formed at least partially from a resiliently compressible material that is configured to regulate a closure pressure between the jaw members.

9. The forceps according to claim 8, wherein the closure pressure between the jaw members is in the range of about 3 kg/cm$^2$ to about 16 kg/cm$^2$.

10. The forceps according to claim 1, wherein the stop member is removably engagable within the first channel of the at least one jaw member via friction-fitting.

\* \* \* \* \*